United States Patent [19]

Guth et al.

[11] Patent Number: 4,515,597
[45] Date of Patent: May 7, 1985

[54] MAGNESIUM COMPLEXES OF OLIGOMERIC PHOSPHONIC ACID ESTERS, A PROCESS FOR THEIR PREPARATION AND THEIR USE AS STABILIZERS IN ALKALINE, PEROXIDE-CONTAINING BLEACH LIQUORS

[75] Inventors: Christian Guth, Basel; Paul Schäfer, Riehen, both of Switzerland

[73] Assignee: Ciba Geigy Corporation, Ardsley, N.Y.

[21] Appl. No.: 557,012

[22] Filed: Dec. 1, 1983

[30] Foreign Application Priority Data

Dec. 10, 1982 [CH] Switzerland ............... 7216/82
Jan. 25, 1983 [CH] Switzerland ................ 400/83

[51] Int. Cl.$^3$ ............... C07F 9/40; C11D 3/39; D06L 3/02
[52] U.S. Cl. ............... 8/107; 252/180; 252/186.25; 252/186.28
[58] Field of Search ............... 252/186.25, 186.28; 8/107

[56] References Cited

U.S. PATENT DOCUMENTS

| | | | |
|---|---|---|---|
| 2,838,459 | 6/1958 | Sprout | 8/111 |
| 3,122,417 | 2/1964 | Blaser et al. | 252/186.31 |
| 3,562,169 | 2/1971 | Prentice | 252/174.16 |
| 3,621,081 | 11/1971 | Prentice | 252/142 |
| 3,687,627 | 8/1972 | Stalter | 423/273 |
| 3,740,187 | 6/1973 | Kowalski | 8/111 |
| 3,860,391 | 1/1975 | Kling et al. | 252/186.25 |
| 3,951,594 | 4/1976 | Smolens | 8/111 |
| 4,061,695 | 12/1977 | Tai et al. | 252/80 |
| 4,148,603 | 4/1979 | Schwuger et al. | 8/137 |
| 4,201,669 | 5/1980 | Becker et al. | 210/58 |
| 4,253,912 | 3/1981 | Becker et al. | 162/76 |
| 4,253,969 | 3/1981 | Becker et al. | 210/699 |
| 4,254,063 | 3/1981 | Becker | 260/931 |

FOREIGN PATENT DOCUMENTS 0029076 5/1981 European Pat. Off. .
2828416 1/1979 Fed. Rep. of Germany .

*Primary Examiner*—A. Lionel Clingman
*Attorney, Agent, or Firm*—Edward McC. Roberts; Kevin T. Mansfield

[57] ABSTRACT

Magnesium complexes of oligomeric phosphonic acid esters of the formula

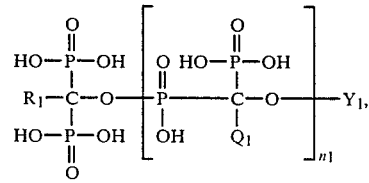

in which $Y_1$ is hydrogen or $-COT_1$, $R_1$, $Q_1$ and $T_1$ are alkyl and $n_1$ is 1 to 16, are particularly suitable, in combination with polyhydroxy compounds, for use as stabilizers in alkaline, peroxide-containing bleach liquors for bleaching fibrous material made of or containing cellulose.

13 Claims, No Drawings

MAGNESIUM COMPLEXES OF OLIGOMERIC PHOSPHONIC ACID ESTERS, A PROCESS FOR THEIR PREPARATION AND THEIR USE AS STABILIZERS IN ALKALINE, PEROXIDE-CONTAINING BLEACH LIQUORS

Oligomeric phosphonic acid esters of the formula

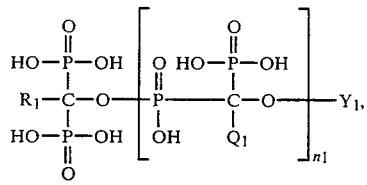
(1)

in which $Y_1$ is hydrogen or $-COT_1$, $R_1$, $Q_1$ and $T_1$ are each alkyl having 1 to 4 carbon atoms and $n_1$ is 1 to 16, are known from European Patent Application No. 29,076. They are used to prevent the formation of water-insoluble salts in aqueous systems.

It has now been found that magnesium complexes of these oligomers are very suitable for stabilising alkaline, peroxide-containing bleach liquors for bleaching fibrous material made of or containing cellulose.

The present invention therefore relates to magnesium complexes containing, as ligands, oligomeric phosphonic acid esters of the above formula (1).

The present invention also relates to a process for the preparation of the magnesium complexes, to the bleach liquors containing these complexes, to the use of these liquors for bleaching fibrous material made of or containing cellulose, to processes for bleaching fibrous material made of or containing cellulose and to the materials bleached by means of these processes.

Alkyl radicals suitable for $R_1$, $Q_1$ and $T_1$ in the compounds of the formula (1) are isobutyl, preferably isopropyl, especially n-butyl and n-propyl and, in particular, ethyl and methyl, methyl being particularly preferred.

If $Y_1$ is $-CO-T_1$, $T_1$ and $R_1$ preferably have the same meanings. Hydrogen is, however, the meaning of $Y_1$ which is of primary interest. Preferred limiting values of $n_1$ are 1 to 16 and, in particular, 1 to 12, and oligomers having average values of n of about 5 to 9, preferably about 5 or 6, form the main constituent in the mixture. Oligomers in which n=1 and oligomers in which n=12 to 16, especially 12, are, however, always present in minor amounts in the mixture.

It is preferable to use oligomers of the formula

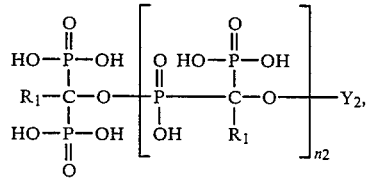
(2)

in which $Y_2$ is hydrogen or $-CO-T_1$, $n_2$ is 1 and 14 and $T_1$ is as defined, and in particular, those of the formula

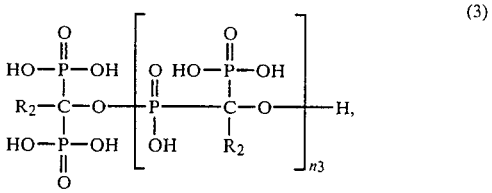
(3)

in which $R_2$ is methyl or ethyl and $n_3$ is 1 to 12.

The preparation of the magnesium complexes according to the invention is effected by reacting a, preferably aqueous, solution of the said oligomers with a water-soluble magnesium salt, for example magnesium acetate, sulfate or oxide or, preferably, magnesium chloride. Preferably, an aqueous solution of said oligomers is dropwise added to an aqueous solution of said magnesium salt at room temperature (15°–25° C.) while stirring. The pH-value of the mixture obtained is in the range of from 0 to 1. The oligomer solutions used contain, as a rule, 30 to 55, preferably 30 to 40, % by weight of phosphonic acid esters. Magnesium chloride is generally employed in the form of its hexahydrate ($MgCl_2.6H_2O$). However, it is also possible to use magnesium chloride of a lower water content as well as anhydrous magnesium chloride. The molecular weight ratio of phosphonic acid ester to magnesium ($Mg^{2+}$) is preferably 1:0.1 to 1:4.5. A molar ratio of 1:0.5 to 1:3.0 is particularly suitable. (A molecular weight of 394 is arbitrarily chosen for the phosphonic acid esters, in which case $n_1$ is then 1, $R_1$ and $Q_1$ are methyl and $Y_1$ is hydrogen, in the compounds of the formula (1)). The heat of reaction formed in the preparation of the magnesium complexes can be removed by cooling with conventional means.

The bleach liquors according to the invention (aqueous solutions) for bleaching cellulosic materials generally contain:

(a) an alkali metal hydroxide,
(b) hydrogen peroxide,
(c) a magnesium complex of the oligomers of the formula (1),
(d) a polyhydroxy compound and, optionally, as further additives,
(e) a peroxydisulfate,
(f) a wetting agent,
(g) an anti-foaming and/or deaerating agent,
(h) a water-soluble alkali metal salt of a silicate and-/or
(i) an optical brightener.

Potassium hydroxide and, in particular, sodium hydroxide, which is cheaper, and hydrogen peroxide, in particular in the form of aqueous, preferably concentrated (for instance 30 to 50 percent by weight) solutions thereof, are employed as the components (a) and (b). The component (a) can, however, also be employed in the form of a solid, for example caustic soda.

The magnesium complexes, according to the invention, of the oligomeric phosphonic acid esters, component (c), suppress very effectively the decomposition of the hydrogen peroxide when raw cotton is introduced into the bleach liquor. This stabilising effect is also effective if the temperature of the bleach liquor is raised. The magnesium complexes are also suitable for another variant of this process, known as hot bleaching (in contrast to cold bleaching), in which the fibre material which has been impregnated with the bleach liquor is, for example, treated at an elevated temperature. In the case of hot bleaching it is preferable to employ complexes having a higher content of magnesium. For example, complexes containing the oligomer and magnesium in a molar ratio of 1:2 to 1:4.5 are suitable.

The polyhydroxy compounds (d) ensure, in particular even at pH values exceeding 11, a considerable stabilising effect on the bleach liquor according to the invention. Suitable polyhydroxy compounds are compounds containing at least 2 hydroxyl groups. Preferably these compounds have the formula

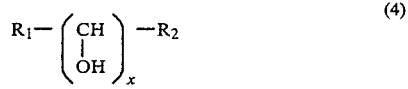  (4)

in which $R_1$ and $R_2$ independently of one another are —$CH_2OH$, —CHO or —$CO_2M$, M is hydrogen or an alkali metal, preferably sodium, and x is 2 to 5, preferably 2 to 4.

Further preferred compounds of the formula (4) are the hydroxycarboxylic acids of the formula

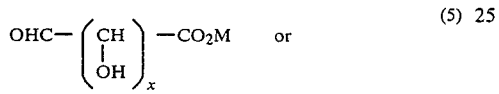  (5)

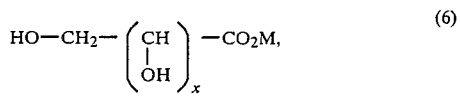  (6)

in which M and x are as defined, or a lactone of these hydroxycarboxylic acids. Gluconic acid and its alkali metal salts, preferably sodium salts (Na gluconate), and also the γ-lactone of gluconic acid, give particularly good results. It is preferable to employ 0.1 to 20 mol of polyhydroxy compound to 1 mol of phosphonic acid ester. Suitable bleach liquors thus contain 0.4 to 10 g/liter of polyhydroxy compound.

Preferred components (e) are alkali metal peroxodisulfates and, in particular, sodium peroxodisulfate ($Na_2S_2O_8$), which is preferably employed in solid form.

Suitable wetting agents (f) are not only anionic surfactants, but, in particular, also mixtures thereof with nonionic surfactants. Examples of preferred anionic surfactants are alkanesulfonates, alkylarylsulfonates, fatty acid condensation products, protein cleavage products or salts thereof and, in particular, alkylsulfate salts and alkylbenzenesulfonic acids having 12 to 22 carbon atoms in the alkyl radical. Examples of preferred nonionic surfactants are adducts formed from alkylene oxides, in particular propylene oxide and especially ethylene oxide, and alkylphenols having, for example, 4 to 12 carbon atoms in the alkyl radical, in particular fatty acid amides and especially fatty alcohols, adducts formed from ethylene oxide and fatty alcohols being particularly preferred, and being of primary interest in the form of a mixture with the alkylsulfates, alkanesulfonates, and alkylbenzenesulfonic acids of the type indicated. Further suitable components in these mixtures are silicone surfactants or silicone oils.

Higher alcohols, for example isooctyl alcohol, but especially anti-foaming and/or deaerating agents based on silicones, are suitable as the preferred component (g).

It is preferable to combine the components (f) and (g) with commercially available aqueous formulations, of about 10 to 60, preferably 30 to 40, percent by weight, of non-foaming surfactant mixtures.

Water-soluble alkali metal silicates, especially soda water glass having a content of 24 to 28% of $SiO_2$, especially in the form of aqueous solutions containing about 30 to 40 percent by weight, are, for example, suitable as the preferred component (h).

The optical brighteners employed as the component (i) generally belong to the styryl and stilbene series, for example distyrylarylenes, diaminostilbenes, ditriazolylstilbenes, phenylbenzoxazolylstilbenes, stilbenenaphthotriazoles and dibenzoxazolylstilbenes. Preferred optical brighteners are those of the type of distyrylbiphenyls or bistriazinylaminostilbenes containing sulfonic acid groups, for example sulfonated distyrylbiphenyl and bistriazinyl derivatives, in particular the bis-(phenylaminodialkylamino-s-triazinyl)-stilbenedisulfonic acids and bis-(phenylaminomorpholino-s-triazinyl)-stilbenedisulfonic acids present in the form of alkali metal salts, especially potassium salts or preferably sodium salts. These are preferably employed in the form of commercially available aqueous liquid formulations containing about 20 to 30 percent by weight.

The bleach liquors according to the invention preferably contain:
0.02 to 10 percent by weight (0.2 to 100 g/liter) of the component (a),
0.01 to 2.5 percent by weight (1.0 to 70 g/liter) of the component (b),
0.02 to 4 percent by weight (0.3 to 25 g/liter) of the component (c),
0.04 to 1 percent by weight (0.4 to 10 g/liter) of the component (d),
and, if appropriate,
0 to 5 percent by weight (0 to 50 g/liter) of the component (e),
0 to 2.5 percent by weight (0 to 50 g/liter) of the component (f),
0 to 0.05 percent by weight (0 to 10 g/liter) of the component (g),
0 to 1.5 percent by weight (0 to 42.8 g/liter) of the component (h), and/or
0 to 0.8 percent by weight (0 to 32 g/liter) of the component (i),
the percentages relating in each case to the content of active substance in the components (a) to (i).

Particularly suitable bleach liquors contain 0.05 to 0.5, in particular 0.05 to 0.3, percent by weight (0.5 to 5, in particular 0.5 to 3, g/liter) of the component (c), and 0.04 to 0.5, in particular 0.04 to 0.35, percent by weight (0.4 to 5, in particular 0.4 to 3.5, g/liter) of the component (d).

The application processes for the alkaline, oxidative bleaching of fibrous material made of or containing cellulose, using the bleach liquors according to the invention, are carried out by methods known per se.

In this connection, a distinction is drawn between treatment in long liquors and the so-called padding or impregnation processes.

In long liquors, the material is subjected to treatment for about 1 to 3 hours at elevated temperature at a liquor ratio of about 1:3, for example in a jigger, or up to about 1:40, for example in a winch, the treatment temperature being about 40° to 140° C., preferably 60° to 100° C., under normal conditions, i.e. under atmospheric pressure, or above 100° C., preferably 105° to 140° C., under so-called HT (i.e. high temperature) conditions.

In the padding processes, the material to be treated is impregnated by being immersed in the padding liquor and subsequently squeezed out, the padding liquor having, as a rule, a temperature of 20° to 95° C. The chemicals applied by the impregnation process then act on the textile material, the treatment time, the, if appropriate increased, temperature and the concentration of the chemicals being directly related, and the conditions selected being dependent on the nature of the fibre material and, in particular, on the apparatus available. Thus, depending on the equipment used, the fibre material is treated in the form of a web or hank, for example, at about 100° to 140° C. for 1 to 10 minutes in steamers, at about 95° to 100° C. for about 8 to 30 minutes in open-width J-boxes, at about 90° to 100° C. for about 45 minutes to 2 hours in ordinary J-boxes or conveyors, at about 80° to 90° C. for about 2 to 4 hours in the pad-roll process or at about 50° to 80° C. for about 3 to 6 hours, or at about 20° to 30° C. for about 10 to 24 hours, in the pad-batch process, the duration of treatment being in general the shorter, the higher the temperature.

The fibre materials are then as a rule thoroughly washed, first with boiling hot water, then with warm water and finally with cold water, if necessary neutralised with, for example, acetic acid and finally freed from water and dried.

The cellulose-containing material which is bleached in accordance with the invention can be in a very wide variety of stages of processing, for example in the form of loose material, yarn or woven or knitted fabric. The material is, therefore, as a rule always textile fibre material which has been produced from pure textile cellulose fibres or from mixtures of textile cellulose fibres and textile synthetic fibres.

Examples of suitable cellulosic fibres are those composed of regenerated cellulose, for example staple rayon and viscose, and those composed of natural cellulose, for example hemp, linen and jute and especially cotton, while examples of suitable synthetic fibres are those composed of polyacrylonitrile and especially polyester and polyamide.

Fabrics composed of cotton or regenerated cellulose or mixed fabrics composed of cotton and polyester and of cotton and polyamide are particularly suitable for being bleached in accordance with the invention, cotton woven and knitted fabrics being of primary interest. Materials which have been pre-washed with, for example, surfactants are also suitable. It is also possible to bleach sized cotton fibres, bleaching being carried out after or before desizing.

The fibre materials which have been bleached in accordance with the invention are distinguished by freedom from husks, good re-wettability, low ash content and, in particular, a high degree of whiteness. In addition, the cellulose, or the cellulose component, of the bleached material does not exhibit any damage or any substantial degradation of the degree of polymerisation of the cellulose (AP degree, AP=average polymerisation).

A particularly high stabilising action, in particular at high pH values (>11) is achieved by the use of the combination, according to the invention, of magnesium complexes and polyhydroxy compounds. The active oxygen content originally present in the bleach liquors is maintained for a prolonged period or decreases only to an insubstantial extent. In spite of this, the bleaching effect is excellent. The liquors are stable and can be used for a prolonged period. In addition, it is possible in some cases to dispense completely with silicates (water glass) by using the magnesium complexes, so that hardly any incrustation of the bleaching equipment or incrustations on the bleached fibre material, or none at all, are formed.

It has also been found that, as the concentration of alkali metal hydroxide in the bleach liquor increases, it is also possible to stabilise a similarly increasing concentration of active oxygen.

The advantageous properties mentioned, which are shown by the combinations, according to the invention, of magnesium complexes and polyhydroxy compounds in bleach liquors, can manifest themselves, for example, in a simplification or intensification of the bleaching processes. In cold storage bleaching, for example, a higher content of active oxygen remains on the treated goods, and it is then also possible to utilise the bleaching power of this active oxygen in the washing process with hot water which follows the cold storage bleaching. This washing process can, therefore, be regarded as a (silicate-free) hot bleach, and the whole process, including cold storage bleaching, thus constitutes a two-stage bleaching process. Materials treated in this way are distinguished by a very high degree of whiteness.

In the examples which follow, percentages and parts are always by weight, unless stated otherwise.

EXAMPLE 1

560.4 g of a 35% aqueous solution of the oligomer of the formula

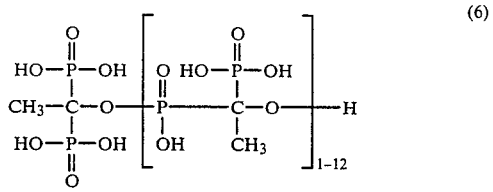

are adjusted to a pH-value of 5 with a 50% aqueous solution of potassium hydroxide, with cooling. 202.1 g of magnesium chloride hexahydrate are then added. This gives an aqueous solution of a magnesium complex in which the molar ratio of oligomer of the formula (6) to magnesium ($Mg^{2+}$) is 1:2.

A bleach liquor is prepared, containing, per liter of aqueous solution, 10 ml of the complex solution prepared above, 20 ml of 30% sodium hydroxide solution, 40 ml of 35% hydrogen peroxide, 5 g of a 25% aqueous surfactant solution composed of 56% of a ($C_{12}$-$C_{22}$)-alkylbenzenesulfonic acid, 25% of ethylene oxide adducts with technical ($C_{12}$-$C_{22}$)-fatty alcohol mixtures and 19% of sodium ($C_{12}$-$C_{22}$)-alkylsulfate and one further gram of magnesium chloride hexahydrate. The ratio of oligomer to magnesium in the complex now present is 1:3.

This liquor is heated to 90° C. 10 g of raw cotton fabric are introduced (liquor ratio 1:50), and bleaching is carried out for 15 minutes.

This gives a fabric which has been bleached to a high degree of whiteness and is free from husks.

After this treatment, the residual content of peroxide is still 80%. This bleaching liquor can be used for further bleaching processes; it is normally unusable when the concentration of hydrogen peroxide has fallen below about 20%. If 2.1 g/liter of oligomers of the formula (6) are used instead of the magnesium complex, the hydrogen peroxide present in the liquor decomposes spontaneously and substantially. The residual content of peroxide after the bleaching process is only 9%.

A good bleaching action is also achieved if bleaching is carried out with the bleach liquor described at only 60° C. The residual content of peroxide in the liquor is then still more than 80%.

Both a good bleaching effect and a high residual content of peroxide can also be recorded if the said bleach liquor contains only 10 ml/liter of 30% sodium hydroxide solution and 20 ml/liter of 35% strength hydrogen peroxide.

EXAMPLE 2

A raw cotton fabric is impregnated with an aqueous bleach liquor containing, per liter, 50 g of sodium hydroxide, 60 ml of 35% hydrogen peroxide, 5 g of sodium peroxodisulfate, 5 g of the surfactant solution used in Example 1 and 15 ml of an aqueous solution composed of 112.5 parts of the 35% aqueous solution of the oligomers of the formula (6), 40.1 parts of a 50% aqueous solution of potassium hydroxide and 10.1 parts of magnesium chloride hexahydrate, and the fabric is squeezed out to a liquor pick-up of 100%. The impregnated fabric is rolled up and, packaged in polyethylene sheeting, is stored in the wet state for 24 hours at room temperature. The fabric is then rinsed with hot (90°–98° C.) water and then with cold water (5°–25° C.) and is then dried.

The degree of whiteness of the raw fabric is thus increased from −62 to 60 (CIBA-GEIGY whiteness scale).

The peroxide content of the impregnating liquor used is still 98% after 24 hours.

EXAMPLE 3

A raw cotton fabric is impregnated with an aqueous bleach liquor containing, per liter, 60 g of sodium hydroxide, 60 ml of 35% hydrogen peroxide, 4 g of sodium peroxodisulfate, 5 g of the surfactant solution used in Example 1 and 15 ml of an aqueous solution consisting of 100 parts of the 35% aqueous solution of the oligomers of the formula (6), 62 parts of magnesium chloride hexahydrate, 158 parts of sodium gluconate and 680 parts of water, and the fabric is squeezed out to a liquor pick-up of 100%. The impregnated fabric is rolled up and, packaged in polyethylene sheeting, is stored in the wet state for 24 hours at room temperature. The fabric is then rinsed, first with hot (90°–98° C.) water and then with cold water (5°–25° C.) and is subsequently dried.

The degree of whiteness of the treated raw fabric is increased from −62 to 45 (CIBA-GEIGY whiteness scale). This gives a fabric which has been bleached to a high degree of whiteness and is free from husks.

The peroxide content of the impregnating liquor used is still 98% after 24 hours. A peroxide content of 28% (100% at the start of storage) can still be detected on the impregnated fabric after storage for 24 hours at room temperature. This suggests a trouble-free bleaching process.

Good results are also obtained if glucose, gluconic acid or the γ-lactone thereof is employed instead of the sodium gluconate.

EXAMPLE 4

A bleach liquor (a) is prepared, containing, per liter, 4 g of sodium hydroxide, 20 ml of 35% hydrogen peroxide, 6 g of 35% sodium silicate solution, 1 g of an aqueous solution containing 31.9% of sodium pentadecanesulfonate and 10.4% of an adduct of a $C_{12}$-olefine alcohol with 4 mol of ethylene oxide, and 6 g of an aqueous composition containing 20% of a 35% aqueous solution of the compounds of the formula (6), 14.5% of magnesium chloride hexahydrate and 15.5% of glucose.

A second bleach liquor (b) is prepared, containing only 0.2 g/liter of magnesium chloride hexahydrate instead of the 6 g/liter of aqueous composition.

100 ml portions of the liquors (a) and (b) are heated to 90° C. 5 pieces of raw cotton fabric (5 g) are treated successively in each of the liquors. The immersion time is 15 minutes in each case. After the 5th cotton fabric has been bleached, its degree of whiteness (CIBA-GEIGY whiteness scale) and the residual content of peroxide in the liquors (a) and (b) is determined (in comparison with the peroxide content of the corresponding cold preparations):

Bleach liquor (a): residual content of peroxide 66%, degree of whiteness 38

Bleach liquor (b): residual content of peroxide 21%, degree of whiteness 24

(Comparison: raw cotton, degree of whiteness −63)

It has thus found that peroxide is stabilised surprisingly well in the bleach liquor (a) according to the invention. Furthermore, the cotton fabric which has been treated in accordance with the invention has a high degree of whiteness.

EXAMPLE 5

A mixed fabric composed of 33 parts of raw cotton and 67 parts of polyester is impregnated with an aqueous bleach liquor containing, per liter, 30 g of sodium hydroxide, 50 ml of 35% hydrogen peroxide, 4 g of sodium peroxodisulfate, 5 g of the surfactant solution used in Example 4 and 10 g of an aqueous composition containing 10% of a 35% aqueous solution of the compounds of the formula (6), 5.4% of magnesium chloride hexahydrate and 15.5% of sodium gluconate, and the fabric is squeezed out to a liquor pick-up of 100%. The mixed fabric impregnated in this way is packaged in plastic sheeting in an airtight manner and is stored for 24 hours at room temperature. The fabric is then washed with boiling water, hot water and then cold water, for 1 minute in each case, and is neutralised and dried. The degree of whiteness of the bleached fabric has increased from 5 to 63 (CIBA-GEIGY whiteness scale).

EXAMPLE 6

A mixed knitted fabric composed of 47 parts of raw cotton and 53 parts of polyamide 6,6 is treated for 1 hour in a bleach liquor (liquor ratio 1:20) which has been heated to 85° C. and contains, per liter, 5 ml of 35% hydrogen peroxide, 0.15 g of Proventin 7 (Degussa trademark), 1 g of the surfactant solution used in Example 5, 2 g of the aqueous composition used in Example 5 and sufficient sodium hydroxide solution to give the bleach liquor a pH-value of 10.5. The mixed knitted fabric which has been treated in this way is washed with boiling water, hot water and cold water, for 1 minute in each case, and is neutralised and dried. The degree of whiteness of the bleached knitted fabric has increased from −71 to 37 (CIBA-GEIGY whiteness scale).

EXAMPLE 7

A bleach liquor is prepared, containing, per liter, 20 g of sodium hydroxide solution, 50 ml of 35% hydrogen peroxide, 10 g of the aqueous composition used in Example 6 and 5 g of the surfactant solution used in Example 6. The pH-value of this bleach liquor is 12.1.

A second bleach liquor is prepared, containing the said components in five times the concentration.

After 24 hours storage at room temperature, both bleach liquors still have their original content of hydrogen peroxide.

We claim:

1. An alkaline bleach liquor containing
   (a) a peroxide bleach
   (b) a magnesium complex which contains, as ligands, oligomeric phosphonic acid esters of the formula

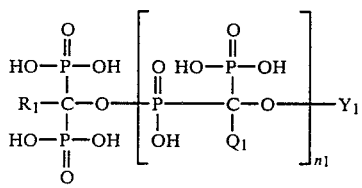

in which $Y_1$ is hydrogen or $-COT_1$, $R_1$, $Q_1$ and $T_1$ are each alkyl having 1 to 4 carbon atoms and $n_1$ is 1 to 16, and
   (c) a polyhydroxy compound containing at least 2 hydroxyl groups.

2. The bleach liquor of claim 1, wherein component (c) is of the formula

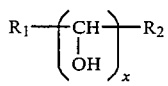

in which $R_1$ and $R_2$ independently of one another are $-CH_2OH$, $-CHO$ or $-CO_2M$ is hydrogen or an alkali metal and x is 2 to 5.

3. The bleach liquor of claim 2, wherein $R_1$ is $-CH_2OH$ and $R_2$ is $CO_2M$ and wherein this hydroxy carboxylic acid can be in lactone form.

4. The bleach liquor of claim 2, wherein component (c) is glucose, gluconic acid, an alkali metal salt of gluconic acid or the γ-lactone of gluconic acid.

5. The bleach liquor of claim 1, wherein the molar ratio of oligomeric phosphonic acid ester:magnesium:-polyhydroxy compound is in the range of 1:(0.1–4.5):(0.1–20).

6. The bleach liquor of claim 1, wherein component (a) is hydrogen peroxide.

7. The bleach liquor of claim 6, which additionally contains a peroxodisulfate, a wetting agent, an anti-foaming and/or deaerating agent, a water-soluble alkali metal salt of a silicate, and/or an optical brightener.

8. The bleach liquor of claim 6, containing 0.02 to 10 percent by weight of alkali metal hydroxide, 0.01 to 2.5 percent by weight of hydrogen peroxide, 0.02 to 4 percent by weight of component (b), 0.04 to 1 percent by weight of component (c), 0 to 5 percent by weight of a peroxodisulfate, 0 to 2.5 percent by weight of a wetting agent, 0 to 0.05 percent by weight of an anti-foaming and/or deaerating agent, 0 to 1.5 percent by weight of a water-soluble alkali metal silicate and 0 to 0.8 percent by weight of an optical brightener.

9. The bleach liquor of claim 8, containing 0.05 to 0.5 percent by weight of component (b) and 0.04 to 0.5 percent by weight of component (c).

10. The bleach liquor of claim 9, containing 0.05 to 0.3 percent by weight of component (b) and 0.04 to 0.35 percent by weight of component (c).

11. A process for bleaching cellulose fiber material which comprises applying to the material the bleach liquor of claim 1.

12. The process of claim 11, wherein bleaching is carried out at elevated temperature.

13. The process of claim 11, wherein the material is impregnated with the bleach liquor and then steamed at elevated temperature.

* * * * *

UNITED STATES PATENT AND TRADEMARK OFFICE
CERTIFICATE OF CORRECTION

PATENT NO. : 4,515,597
DATED : May 7, 1985
INVENTOR(S) : Christian Guth and Paul Schafer It is certified that error appears in the above-identified patent and that said Letters Patent is hereby corrected as shown below:

Claim 2, Column 9, Line 40 should read--

--$-CH_2OH$, $-CHO$ or $-CO_2M$, M is hydrogen or an alkali --.

Signed and Sealed this

Eighth Day of October 1985

[SEAL]

Attest:

DONALD J. QUIGG

*Attesting Officer*  *Commissioner of Patents and Trademarks—Designate*